(12) United States Patent
Azoulay

(10) Patent No.: US 10,085,814 B2
(45) Date of Patent: Oct. 2, 2018

(54) APPARATUS AND METHOD FOR APPLYING LIGHT IN OCULAR AND PERIOCULAR AREAS

(71) Applicant: LUMENIS LTD., Yokneam Ilit (IL)

(72) Inventor: Kfir Azoulay, Amsterdam (NL)

(73) Assignee: LUMENIS LTD., Yokneam (IL)

( * ) Notice: Subject to any disclaimer, the term of this patent is extended or adjusted under 35 U.S.C. 154(b) by 26 days.

(21) Appl. No.: 15/069,660

(22) Filed: Mar. 14, 2016

(65) Prior Publication Data

US 2016/0193006 A1 Jul. 7, 2016

Related U.S. Application Data

(63) Continuation of application No. 13/707,834, filed on Dec. 7, 2012, now Pat. No. 9,333,370.

(60) Provisional application No. 61/567,859, filed on Dec. 7, 2011.

(51) Int. Cl.
| | | |
|---|---|---|
| *A61B 18/18* | (2006.01) | |
| *A61B 90/00* | (2016.01) | |
| *A61N 5/06* | (2006.01) | |
| *A61F 9/007* | (2006.01) | |
| *A61F 9/008* | (2006.01) | |
| *A61N 5/067* | (2006.01) | |

(52) U.S. Cl.
CPC .............. *A61B 90/04* (2016.02); *A61F 9/008* (2013.01); *A61F 9/0079* (2013.01); *A61N 5/0613* (2013.01); *A61B 2090/049* (2016.02); *A61B 2090/0445* (2016.02); *A61N 2005/067* (2013.01); *A61N 2005/0644* (2013.01); *A61N 2005/0651* (2013.01)

(58) Field of Classification Search
CPC .. A61F 90/04; A61F 90/05; A61F 2090/0436; A61F 2090/0445; A61F 2090/0454; A61F 2090/049; A61F 9/022; A61F 9/025; A61N 5/0613; A61N 5/0616; A61N 5/062; A61N 5/0624; A61N 2005/0644; A61N 2005/0651; A61N 2005/0664; A61N 2005/0665
USPC ....... 606/4–6, 10–13, 16–19; 607/88–91, 96, 607/100, 108, 109; 128/898
See application file for complete search history.

(56) References Cited

U.S. PATENT DOCUMENTS

| | | | |
|---|---|---|---|
| 7,813,790 B2 * | 10/2010 | de Josselin de Jong | ................... A61B 1/247 359/361 |
| 7,886,748 B2 * | 2/2011 | Boxer Wachler | ...... A61B 18/20 128/898 |
| 2002/0111608 A1 | 8/2002 | Baerveldt et al. | |
| 2005/0245916 A1 | 11/2005 | Connor | |

* cited by examiner

*Primary Examiner* — Ahmed Farah
(74) *Attorney, Agent, or Firm* — ISUS Intellectual Property PLL; A. Jason Mirabito

(57) ABSTRACT

A removable tip for alight energy handpiece comprises a hollow conduit configured to surround a light guide in the handpiece; a support extension having a length longer than a length of the hollow conduit; and a shielding extension coupled to the support extension at an angle less than 180 degrees and located in front of the hollow conduit. The shielding extension is configured to be inserted behind an eyelid and extend to the fornix, the shielding extension comprised of a thermally insulative material.

13 Claims, 6 Drawing Sheets

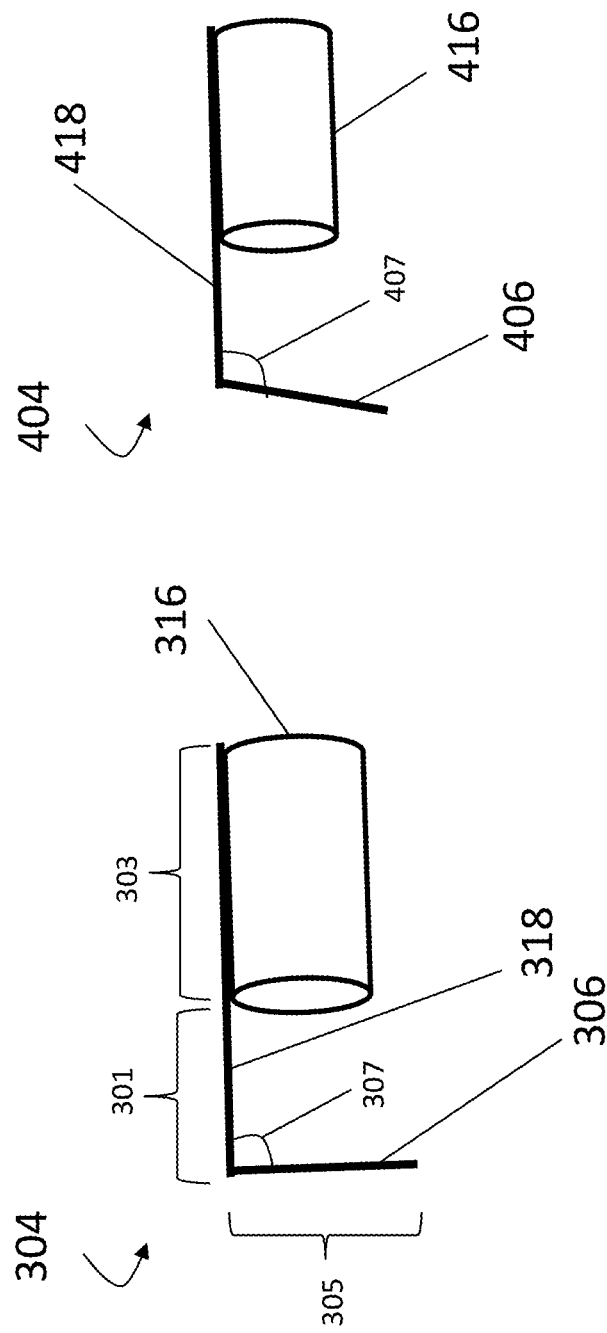

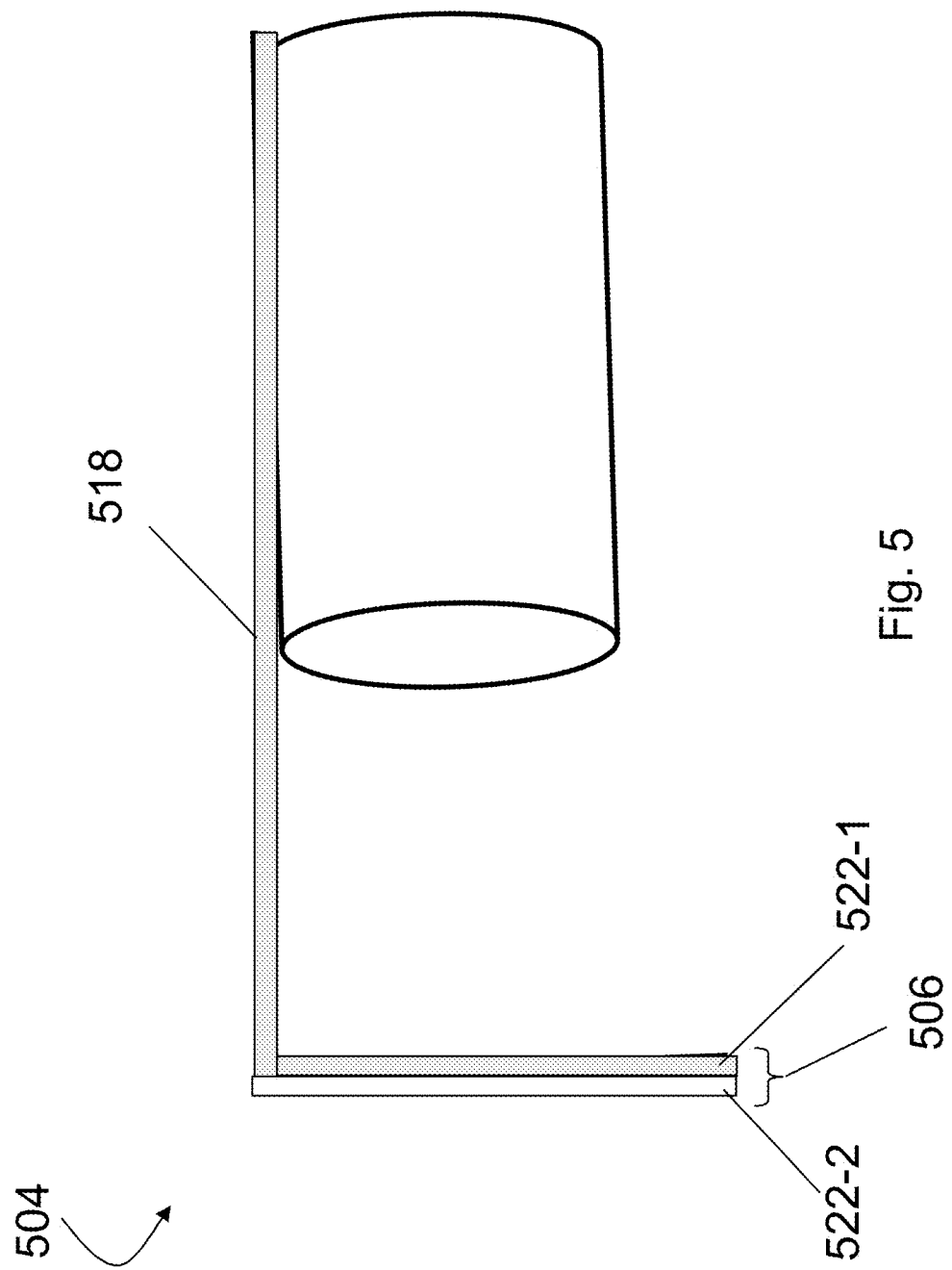

APPARATUS AND METHOD FOR APPLYING LIGHT IN OCULAR AND PERIOCULAR AREAS

RELATED APPLICATION

This application is a continuation application of U.S. patent application Ser. No. 13/707,834, filed Dec. 7, 2012, which claims priority from U.S. Provisional Patent Application Ser. No. 61/567,859, filed Dec. 7, 2011, the entire contents of which are hereby incorporated by reference.

BACKGROUND

Light energy sources, whether incoherent such as LEDs or Intense Pulsed Light (IPL), or coherent, such as a carbon dioxide ($CO_2$) gas laser, Nd:YAG or Er:YAG solid state lasers, fiber or diode lasers, have been used for various applications such as surgical, dermatological and/or aesthetic treatments on areas of skin and various external and internal body organs and tissues. However, using energy sources for application to skin surface areas, particularly in the vicinity of the eye, such as the eyelids and adjacent regions of the face, also referred to as ocular and periocular/circumocular areas, may raise safety concerns. For example, heat dissipation from IPL can cause detrimental damage, either temporary or permanent, to various ocular structures, such as the cornea which is the organ responsible for approximately 70% of the human eye refraction power.

SUMMARY

In one embodiment, a removable tip for an energy light producing handpiece is provided. The removable tip comprises a hollow conduit/cavity configured to surround a light guide in the handpiece; a support extension having a length longer than a length of the hollow conduit/cavity; and a shielding extension coupled to the support extension at an angle less than 180 degrees and located distally to the hollow conduit/cavity. The shielding extension is configured to be inserted behind an eyelid and extend to the fornix, the shielding extension comprised of a thermally insulative material.

DRAWINGS

Understanding that the drawings depict only exemplary embodiments and are not therefore to be considered limiting in scope, the exemplary embodiments will be described with additional specificity and detail through the use of the accompanying drawings, in which:

FIG. 3 is a block diagram of one embodiment of a removable handpiece tip.

FIG. 4 is a block diagram of another embodiment of a removable handpiece tip.

FIG. 5 is a block diagram of yet a further embodiment of a removal handpiece tip.

Figure 1:
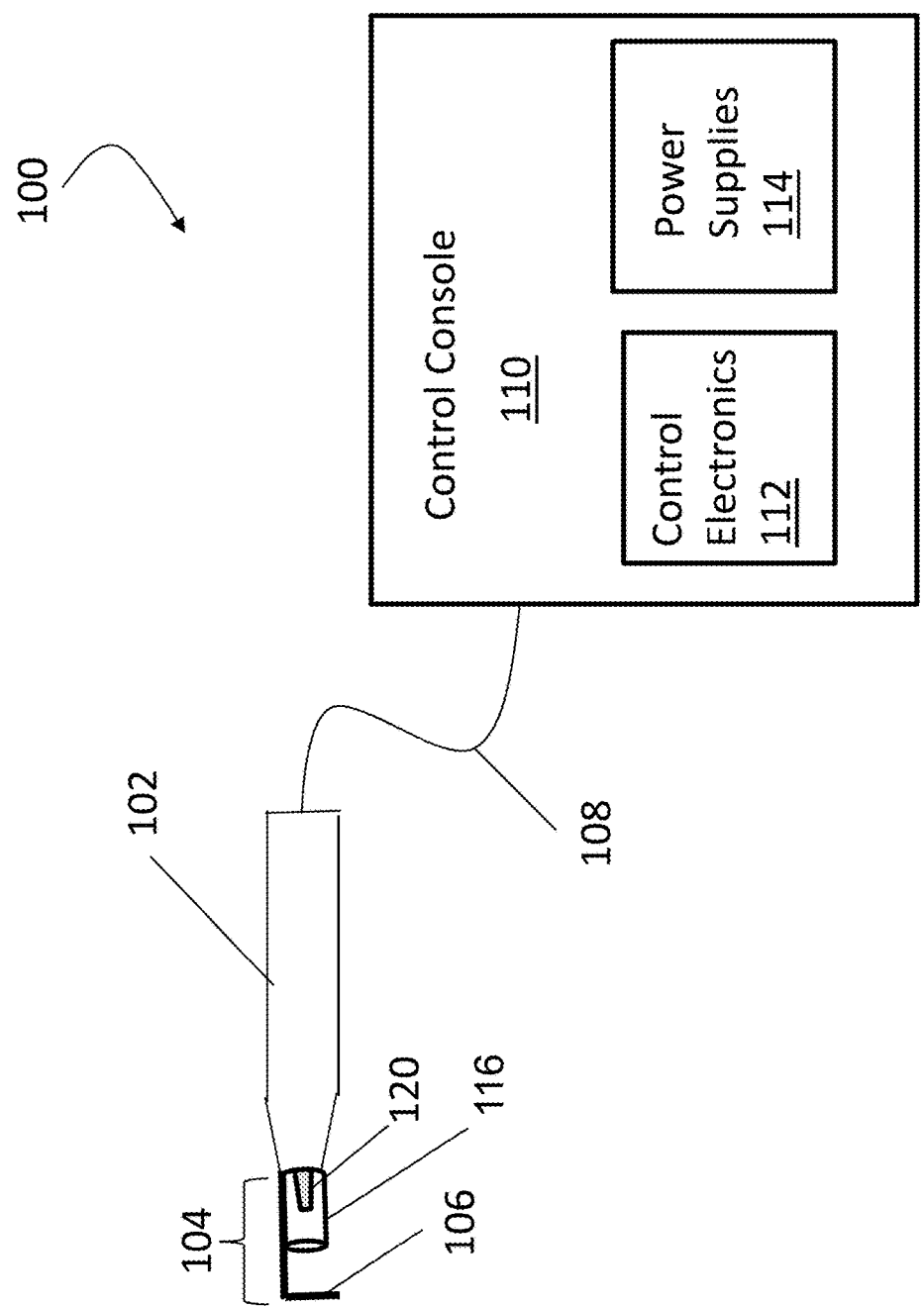
FIG. 1 is a block diagram of one embodiment of a light delivery system.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

The embodiments described below enable safe irradiation of regions of skin covering or surrounding the eye, using various therapeutic energy light sources, such as those mentioned above. In particular, the embodiments described below provide a shield between ocular structures to be protected and the target tissue as described below. Thus, the embodiments described below provide increased protection of sensitive ocular organs as compared to other systems which rely on external protection, such as the system described in U.S. Pat. No. 7,886,748.

FIG. 1 is a high-level diagram of one embodiment of a system 100 for delivering light energy to ocular and periocular areas. System 100 includes a control console 110 and a handpiece 102 coupled to the control console via an umbilical sheath 108. The control console 110 is configured to generate energy at levels appropriate for palpebral treatments. Hence, the control console 110 includes, inter alia, power-supplies and control electronics for components of the handpiece 102. The control electronics 112 and power supplies 114 are connected to the handpiece 102 via the umbilical sheath 108.

The handpiece 102 may include a light guide or crystal 120 for directing the light energy. Handpiece 102 may include an internal light source which is controlled by the control console 110. Internal light sources may be of different types such as LEDs, lamps, diode lasers, fiber lasers or solid state lasers, to name but a few. Multiple sources, whether from the same type or from different types, may be combined into a single handpiece. Light sources located within handpiece 102 have the advantage of using multiple simple umbilical sheaths 108 lacking optical components. In yet another configuration, external light sources may be used. External light sources may be solid state lasers, fiber lasers or gas lasers which may be located in control console 110. In this embodiment, of external light sources, requires the use of an umbilical sheath 108, which among other things, can deliver the light energy from control console 110 to the handpiece 102.

The handpiece 102 may include a conduit/cavity 116 configured to guide the light or accommodate a light guiding element. Different types of light energy sources, such as those mentioned above, may be guided and delivered onto the target tissue in different manners. In one embodiment of the present invention, the handpiece may include a lamp which is configured to generate an intense pulsed light (IPL). In this embodiment a crystal light guide 120 is placed within the handpiece conduit/cavity 116. The crystal light guide 120 may have different lengths and cross sectional geometry. The crystal light guide 120 may have a uniform cross section or the cross section of the light guide 120 may be tapered in order to increase the energy fluence at the spot of treatment. The light guide 120 may also have the same shape and cross section which best conforms to the target tissue area. For example, the light guide 120 may have the same shape as the entire target area so that a single pulse of light may cover the entire treatment target area. A curved crescent-like shape is one which may cover the entire lower eyelid. The light guide 120 may be permanently affixed to the handpiece or may be removably affixed to the handpiece to allow the physician to select the best light guide 120 suited for the patient and treatment area. The light guide 120 may be configured to establish a direct contact with the target tissue or the light guide 120 may treat the target tissue without direct contact. The same light guide 120 may be used in a contact mode or a non-contact mode using an affixing mechanism which supports both configurations.

The light guide 120 may also be configured as a hollowed conduit to deliver light energy in free space to the target tissue. In yet another configuration the light guide may comprise an optical fiber or a bundle of optical fibers. The handpiece 102 may be configured to move the optical fiber in a predetermined pattern such that the fiber will scan at least a portion of the target tissue. Or the handpiece 102 may be configured to scan a light beam through free space over a target tissue using controllable optical elements. A beam splitter may be used in order to create fractional treatment to the target tissue.

The handpiece also includes a removable tip 104. In particular, in some embodiments, the tip 104 is disposable. The size and shape of the tip 104 may vary according to the size and shape of the handpiece 102 to which it is attached. For example, in some embodiments, the tip 104 is configured to be compatible with a small handpiece configured for precise digital manipulation such as the handpiece described in U.S. Pat. No. 7,886,748. However, it is to be understood that other handpiece shapes and configurations can be used in other embodiments. For example, a handpiece having a shape and configuration similar to the handpiece described and shown in U.S. Pat. No. 6,758,845 or D643,530 can be used in other embodiments.

Figure 2:
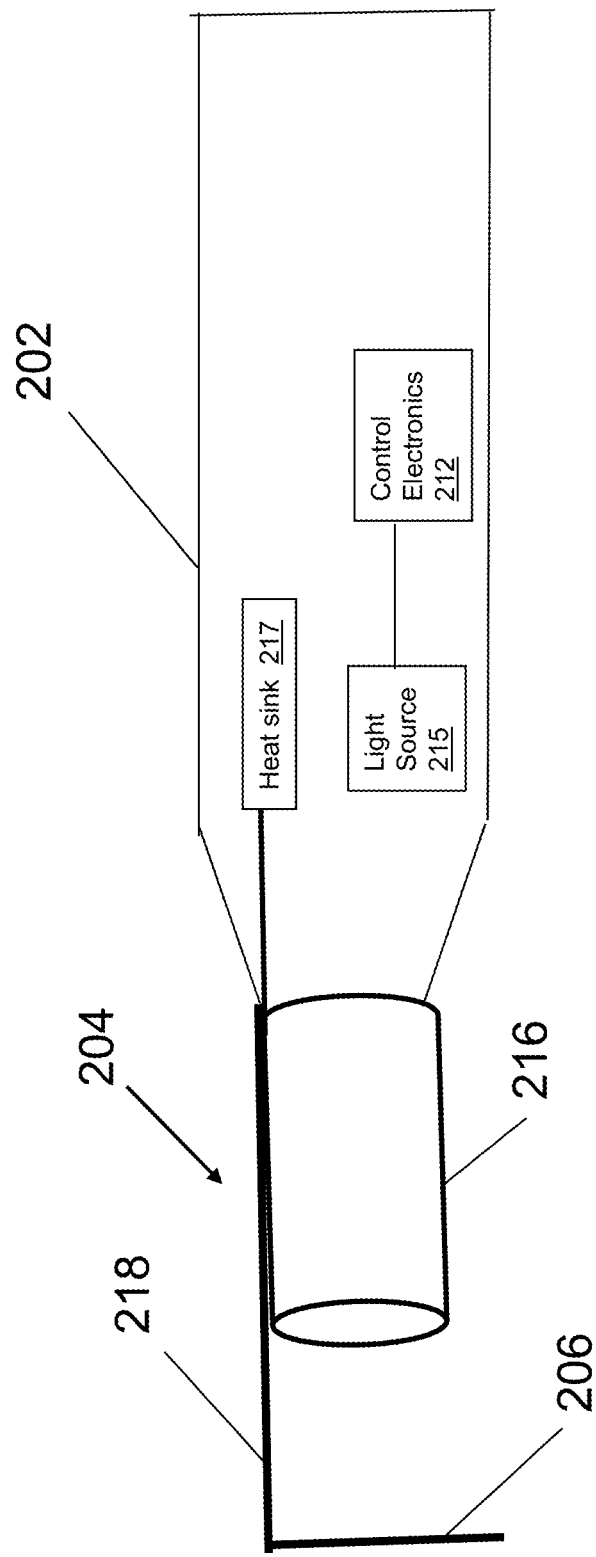
FIG. 2 is a block diagram of one embodiment of a handpiece and handpiece tip.

The tip 104 is physically equipped with a shielding extension 106 which provides protection of sensitive ocular organs. For example, the shielding extension 106 may be configured to create a mechanical separation of the target tissue (e.g. an eyelid) from adjacent posterior structures (e.g. cornea or sclera) and can be used by a medical professional to create an artificial gap or distance between the respective tissues, as described in more detail below. In addition, the shielding extension 106 is made of or coated with thermally insulative materials that prevent thermal energy from dissipating or transferring to other structures which are not the intended target tissue. Furthermore, the tip 104 is made from materials that are biocompatible with ocular tissue such as, but not limited to, collagen and polymer materials that are known to one of skill in the art. Hence, the tip 104 presents minimal to no risk of abrasive damage to the ocular tissue. FIG. 2 is a block diagram of another embodiment of a handpiece 202. In the embodiment of FIG. 2, the control electronics 212, light source 215 and handpiece 202 are combined into a small stand-alone hand-held unit. In such a configuration, the umbilical sheath 108 shown in FIG. 1, may be integrated into the internal electronic circuits of the system and circuitry of the handpiece 102. In addition, the handpiece 102 includes a heat sink 217 that is thermally coupled to the shielding extension 206 via the support extension 218. In this way, thermal energy can be dissipated via the tip 204 to the heat sink 217. Alternatively, the heat sink 217 can be replaced with a cooling source which is thermally coupled to the shielding extension 206 via the support extension 216. In this embodiment, the cooling source is able to cool tissue in contact with the shielding extension 206.

An exemplary tip is described in more detail with respect to FIG. 3. In the example of FIG. 3, the tip 304 comprises the shielding extension 306, a support extension 318, and a hollow conduit/cavity 316. The conduit/cavity 316 prevents accidental contact with a laser guide or crystal in the handpiece used for directing the light energy. In addition, in some embodiments, the length 303 of the conduit/cavity 316 is configured as a distance guide to aid in maintaining a predetermined distance between the surface tissue to be treated and a given crystal in the handpiece. For example, the desired distance between the tissue to be treated and the crystal in the handpiece is dependent on the treatment to be applied and/or on the characteristics of the crystal selected. The length 303 of tip 304, therefore, is manufactured, in some embodiments, to vary from one tip to another tip. Thus, for a given treatment and/or crystal, a tip 304 is selected which has a length 303 that corresponds to the desired distance between the surface tissue and the crystal for the given treatment and/or crystal. In another embodiment of the present invention, a laser light is delivered by handpiece 102 to target tissue via free space and through a conduit in the handpiece and conduit 316 of the tip 304. In this configuration the internal surfaces of the handpiece conduit and the tip conduit 316 are configured to internally reflect the passing light and to minimize energy loss.

In some embodiments in which the length 303 varies from one to tip to another, the length 301 between the shielding extension 306 and the tube 316 is fixed for each tip. For example, the length 301 can be based on the average thickness of an upper or lower adult eyelid. In other embodiments, the length 303 is fixed from one tip to another and the length 301 varies to correspond with desired distances between the surface tissue and the conduit 316.

The shielding extension 306 is configured to be inserted between the ocular conjunctiva and the palpebral conjunctiva and to extend to the fornix. Hence, the length 305 of the shielding extension 306 is based on an average depth of an adult fornix in some embodiments. In other embodiments, the length 305 of the shielding extension can vary from one tip to another such that a medical professional can select a shielding extension having a length appropriate for a given patient. Since the shielding extension extends to the fornix, the shielding extension 306 is also referred to herein as a fornix shield.

In addition to the thermal properties discussed above, the shielding extension 306 is configured to be sufficiently flexible that it can be deformed to define irregular surfaces when inserted. For example, it can deform to the contours of the ocular tissue of a given patient. Thus, the shielding extension 306 is able to prevent energy not absorbed by the target area from reaching tissue behind the target area. In addition, although the angle 307 between the shielding extension 306 and the support extension 318 is depicted as a right angle in FIG. 3, it is to be understood that angle 307 is not limited to a right angle. For example, the angle 307 can change when tip 304 is used due to the deformation of shielding extension 306. In addition, as shown in FIG. 4, the angle 407 formed between the shielding extension 406 and the support extension 418 can be configured with an angle other than 90°.

In some embodiments, the shielding extension 506 may also be constructed from at least two layers, as shown in FIG. 5. Each layer 522-1 and 522-2 has different characteristics. In one embodiment of the present invention, the first layer 522-1 is a proximal layer to the handpiece and the second layer 522-2 is a distal layer of the shielding extension 506. The distal layer 522-2 is configured to be in direct contact with posterior organs to be protected such as cornea or scleara. The proximal layer 522-1 is configured to be in contact with the eyelid. In one embodiment of the present invention, the distal layer 522-1 may have high thermal insulative properties while the proximal layer 522-2 may have high thermal conductivity properties and a low thermal capacity. In this configuration, the proximal layer 522-2 may be used to dissipate thermal energy passed through the eyelid and reach the shielding extension 506. For example, the thermal energy can be dissipated via the shielding extension 506 and support extension 518 to a heat sink reservoir located in the handpiece to which it is thermally coupled. In yet another embodiment, the handpiece 102 may include a cooling source thermally coupled to the proximal layer 522-1 of the shielding extension 506, in order to cool the target tissue. In this embodiment, the distal thermally insulative layer 522-2 isolates and protect posterior organs from cooling energy.

Figure 6:
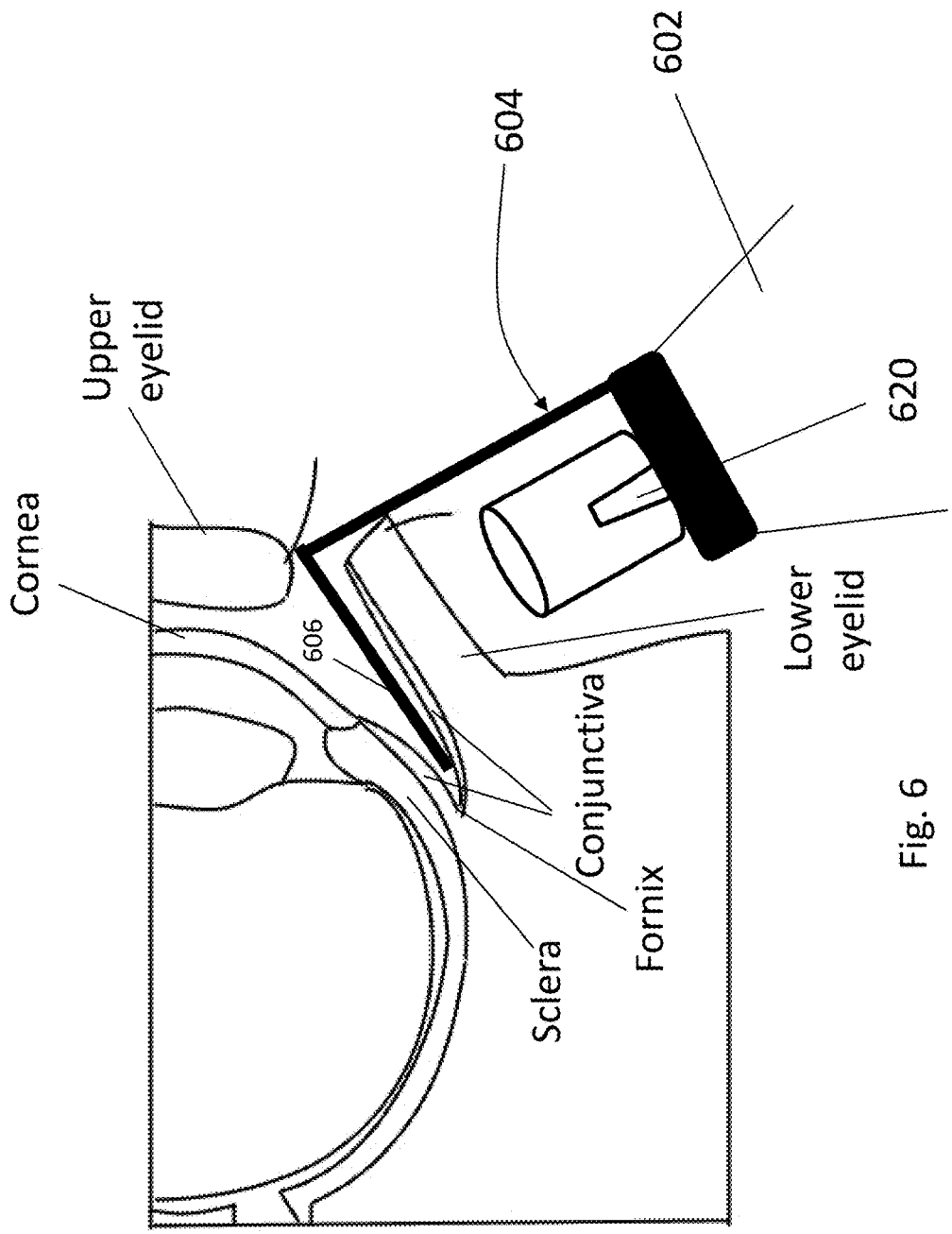
FIG. 6 is an exemplary diagram depicting one embodiment of a removable tip placed to protect ocular tissue.

FIG. 6 depicts an exemplary tip 604 in operation to protect ocular tissue. As shown in FIG. 6, the shielding extension 606 is inserted behind the lower eyelid between the conjunctiva lining the lower eyelid (the palpebral conjunctiva) and the conjunctiva lining the sclera (the ocular conjunctiva). The shielding extension 606 is being inserted toward the fornix. Hence, the shielding extension 606 is able to protect the sclera and the cornea from energy not absorbed by the target tissue in the lower eyelid. In addition, the shielding extension 606 is sufficiently rigid that it can be used to apply a slight force that separates the lower eyelid from the sclera and cornea. Hence, a physical gap is created between the lower eyelid and the sclera/cornea. This physical gap acts as a thermal insulation barrier that provides additional protection from thermal energy. Notably, although the shielding extension 606 is inserted behind the lower eyelid in this example, it is to be understood that the shielding extension 606 can also be inserted behind the upper eyelid.

Figure 7:
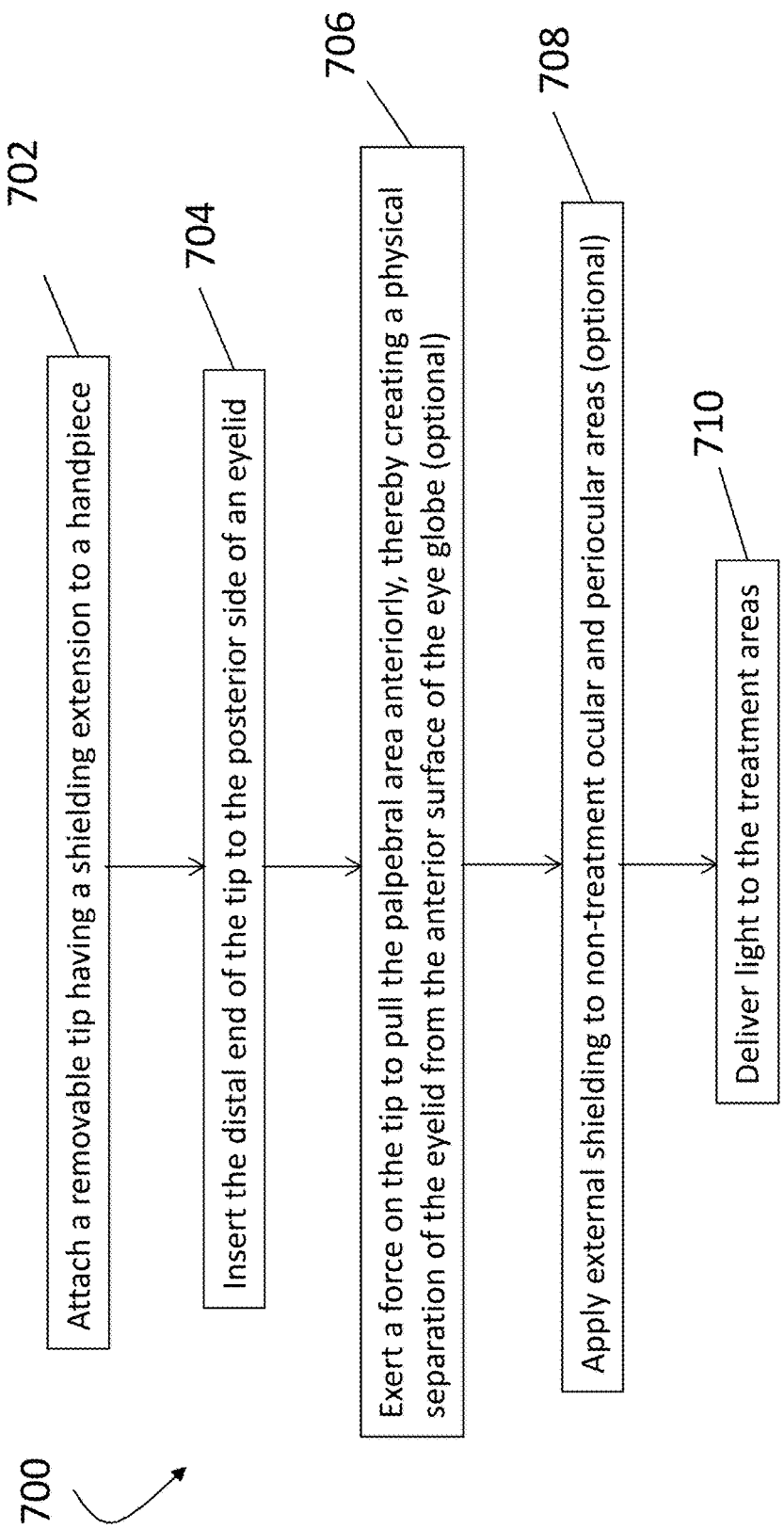
FIG. 7 is a flow chart depicting one embodiment of a method of protecting ocular tissue.

FIG. 7 is a flow chart depicting one embodiment of a method 700 of protecting ocular tissue. Method 700 is implemented using a handpiece having a tip with a shielding extension such as tip 304 described above. At block 702, a removable tip having a shielding extension is attached to a handpiece. At block 704, the distal end of the tip is inserted to the posterior side of an eyelid (e.g. the lower eyelid), in the area between the conjunctiva-covered sclera and the conjunctiva-covered inferior eyelid, until it reaches the fornix, as described above. At block 706, a force is optionally exerted on the tip to pull the palpebral area anteriorly, thereby creating a physical separation of the eyelid from the anterior surface of the eye globe. At block 708, external eye shielding, such as eye shielding described in U.S. Pat. No. 7,886,748, is optionally applied over the non-treated areas of the skin in the ocular and/or periocular areas to provide a second layer of protection.

At block 710, the handpiece delivers light to the ocular and/or periocular treatment areas, such as on an external surface of the eyelid. The handpiece is configured to generate the heat needed for a given treatment. For example, the light can be used to treat a variety of ophthalmic and/or dermatological conditions, such as but not limited to, meibomian gland dysfunction (e.g. dry eye), wrinkles, and lesions in the skin. The light applied by the handpiece is determined based on the condition to be treated. For example, the heat generated to treat meibomian gland dysfunction is generated at a level sufficient to stimulate the meibomian gland and/or decrease palpebral telangiectasia. Thus, the level of heat for treating meibomian gland dysfunction is not necessarily the same as the level to remove wrinkles. In either case, the shielding extension provides thermal protection to the ocular tissue behind the target treatment tissue. In addition, the physical separation created by force exerted on the tip adds another level of protection to the ocular tissue. Thus, the embodiments of the tip described herein provide increased protection of ocular tissue. Furthermore, the tips provide a hygienic solution for protecting the sensitive ocular tissue due to the single-use disposable characteristic of the tip in some embodiments.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A method of protecting ocular tissue during application of light energy, the method comprising:
    providing a handpiece having a light energy device, the handpiece having a tip having a shielding extension configured to be inserted posterior to an eyelid;
    inserting the shielding extension behind the eyelid to the fornix prior to applying light energy to an anterior surface of the eyelid;
    applying light energy from the light energy device to an anterior surface of the eyelid;
    wherein the light energy device is configured to produce intense pulsed light energy; and
    wherein the shielding extension is comprised of a thermally insulative material such that energy not absorbed by a target tissue is prevented from reaching ocular tissue located posterior to the eyelid.

2. The method of claim 1, wherein the shielding extension is configured to be inserted posterior to an eyelid between the ocular conjunctiva and palpebral conjunctiva.

3. The method of claim 1, wherein the tip is a removable tip.

4. The method of claim 3, wherein the removable tip comprises:
    a hollow conduit configured to surround a light guide in the handpiece;
    a support extension having a length longer than a length of the hollow conduit; and
    a shielding extension coupled to the support extension to an angle less than 180 degrees and located distal to the hollow conduit; and
    the shielding extension configured to be inserted behind an eyelid and extend to the fornix, the shielding extension comprised of a thermally insulative material.

5. The method of claim 4, wherein the length of the hollow conduit is configured as a distance guide for maintaining a predetermined distance between the surface tissue to be treated and a crystal light guide in the handpiece.

6. The method of claim 1, wherein the shielding extension is configured to create a mechanical separation of the target tissue from adjacent posterior structures.

7. The method of claim 1, wherein the shielding extension is configured to be flexible such that it can be deformed to define irregular surfaces when inserted.

8. The method of claim 1, wherein the tip comprises a material that is biocompatible with ocular tissue.

9. The method of claim 1, wherein the handpiece further comprises a cooling source thermally coupled to the shielding extension via the support extension.

10. The method of claim 1, wherein the shielding extension is at an angle less than 180 degrees to the tip.

11. The method of claim 1, wherein the shielding extension is at an angle of 90 degrees to the tip.

12. A method of protecting ocular tissue during application of light energy, the method comprising:

providing a handpiece having a light energy device, the handpiece having a tip having a shielding extension configured to be inserted posterior to an eyelid;

inserting the shielding extension behind the eyelid to the fornix prior to applying light energy to an anterior surface of the eyelid;

applying light energy from the light energy device to an anterior surface of the eyelid;

wherein the light energy device is configured to produce intense pulsed light energy; and wherein the shielding extension comprises at least two layers;

wherein a first layer is a proximal layer to the handpiece and the second layer is a distal layer of the shielding extension; and wherein the distal layer is configured to be in direct contact with posterior organs to be protected and the proximal layer is configured to be in contact with the eyelid;

wherein the distal layer has high thermal insulative properties and the proximal layer has high thermal conductivity properties and low thermal capacity.

13. A method of protecting ocular tissue during application of light energy, the method comprising:

providing a handpiece having a light energy device, the handpiece having a tip having a shielding extension configured to be inserted posterior to an eyelid;

inserting the shielding extension behind the eyelid to the fornix prior to applying light energy to an anterior surface of the eyelid;

applying light energy from the light energy device to an anterior surface of the eyelid;

wherein the light energy device is configured to produce intense pulsed light energy; and wherein the handpiece further comprises a heat sink thermally coupled to the shielding extension via the support extension.

* * * * *